United States Patent
Antonioli

(10) Patent No.: US 11,253,140 B2
(45) Date of Patent: Feb. 22, 2022

(54) APPARATUS AND METHOD FOR MONITORING DIFFERENTIAL PRESSURE

(71) Applicant: Hilary C. Antonioli, Plymouth, MI (US)

(72) Inventor: Hilary C. Antonioli, Plymouth, MI (US)

( * ) Notice: Subject to any disclaimer, the term of this patent is extended or adjusted under 35 U.S.C. 154(b) by 830 days.

(21) Appl. No.: 15/924,505

(22) Filed: Mar. 19, 2018

(65) Prior Publication Data

US 2018/0271356 A1    Sep. 27, 2018

Related U.S. Application Data

(60) Provisional application No. 62/474,648, filed on Mar. 22, 2017.

(51) Int. Cl.
*A61B 1/00* (2006.01)
*A61B 1/04* (2006.01)
(Continued)

(52) U.S. Cl.
CPC ...... *A61B 1/00142* (2013.01); *A61B 1/00016* (2013.01); *A61B 1/00018* (2013.01);
(Continued)

(58) Field of Classification Search
CPC ............ A61B 1/00016; A61B 1/00018; A61B 1/00055; A61B 1/00057; A61B 1/00128;
(Continued)

(56) References Cited

U.S. PATENT DOCUMENTS 4,527,551 A  *  7/1985  Ishii ................... A61B 1/00057
                                                       251/149.5
5,938,589 A      8/1999  Wako et al.
(Continued)

FOREIGN PATENT DOCUMENTS

CN         103597340 A       2/2014
DE    102013223376 A1 *   5/2015  ......... A61B 1/00059
(Continued)

*Primary Examiner* — Michael J Carey
*Assistant Examiner* — Stephen Floyd London
(74) *Attorney, Agent, or Firm* — William J. Clemens; Shumaker, Loop & Kendrick, LLP

(57) ABSTRACT

A pressure monitoring device is provided for use with a tool such as a medical endoscope. The device includes a housing which is fluidically coupled with an internal volume of the endoscope. A pump is used to change the pressure inside the device housing and endoscope, thereby establishing a pressure differential from the ambient environment. During an endoscopy procedure, the pressure inside the device housing is monitored, and a change in pressure exceeding a predefined limit causes an alarm signal indicating a leak has occurred in the endoscope. The device housing may be directly mounted to the endoscope, located remotely and connected with a coupling tube, or integrated with an accessory device connected to the endoscope. The pump may be integrated internally to the device housing, or it may be a separate external pump which is connected to the housing. The pressure differential may be positive or negative relative to ambient.

20 Claims, 9 Drawing Sheets

(51) Int. Cl.
*G01M 3/26* (2006.01)
*A61B 90/00* (2016.01)

(52) U.S. Cl.
CPC ...... *A61B 1/00055* (2013.01); *A61B 1/00057* (2013.01); *A61B 1/00128* (2013.01); *A61B 1/00131* (2013.01); *A61B 1/04* (2013.01); *G01M 3/26* (2013.01); *A61B 2090/064* (2016.02); *A61B 2090/0809* (2016.02)

(58) Field of Classification Search
CPC ............ A61B 1/00131; A61B 1/00142; A61B 2090/064; A61B 2090/0809; A61B 2562/0247; A61B 2562/029; G01M 3/26
See application file for complete search history.

(56) References Cited

U.S. PATENT DOCUMENTS

| | | | |
|---|---|---|---|
| 9,693,021 B2 | 6/2017 | Bousquet et al. | |
| 9,699,417 B2 | 7/2017 | Bousquet et al. | |
| 2001/0032494 A1* | 10/2001 | Greszler | A61B 1/00057 73/40 |
| 2004/0118413 A1* | 6/2004 | Williams | A61B 1/125 128/898 |
| 2004/0139789 A1* | 7/2004 | Masters | A61B 1/00055 73/49.2 |
| 2006/0196250 A1* | 9/2006 | Gocho | A61B 1/00057 73/40 |
| 2006/0252991 A1* | 11/2006 | Kubach | G01M 3/26 600/118 |
| 2007/0238923 A1 | 10/2007 | Kubach | |
| 2011/0301414 A1* | 12/2011 | Hotto | A61B 1/00055 600/114 |
| 2012/0000272 A1* | 1/2012 | Soriano Romero | G01M 3/2846 73/40 |
| 2014/0135595 A1 | 5/2014 | Powell et al. | |
| 2014/0238110 A1* | 8/2014 | Williams | A61B 90/70 73/40 |
| 2015/0290403 A1 | 10/2015 | Torisawa et al. | |
| 2015/0290404 A1 | 10/2015 | Torisawa et al. | |
| 2017/0020367 A1 | 1/2017 | Tomita | |
| 2017/0027420 A1* | 2/2017 | Choi | A61B 1/00062 |
| 2018/0084973 A1* | 3/2018 | Terliuc | A61B 1/00126 |
| 2020/0000329 A1* | 1/2020 | Sugaya | A61B 1/015 |
| 2020/0022561 A1* | 1/2020 | Hopkins | A61B 1/00055 |
| 2020/0069152 A1* | 3/2020 | Kasumi | A61B 1/00057 |

FOREIGN PATENT DOCUMENTS

| | | | | |
|---|---|---|---|---|
| EP | 0060548 A1 | | 9/1982 | |
| EP | 3130901 A1 | | 2/2017 | |
| JP | 2006304906 A | * | 11/2006 | ......... A61B 1/00057 |
| JP | 2011005090 A | * | 1/2011 | |
| WO | WO-2019083485 A2 | * | 5/2019 | ......... G01M 3/2846 |

* cited by examiner

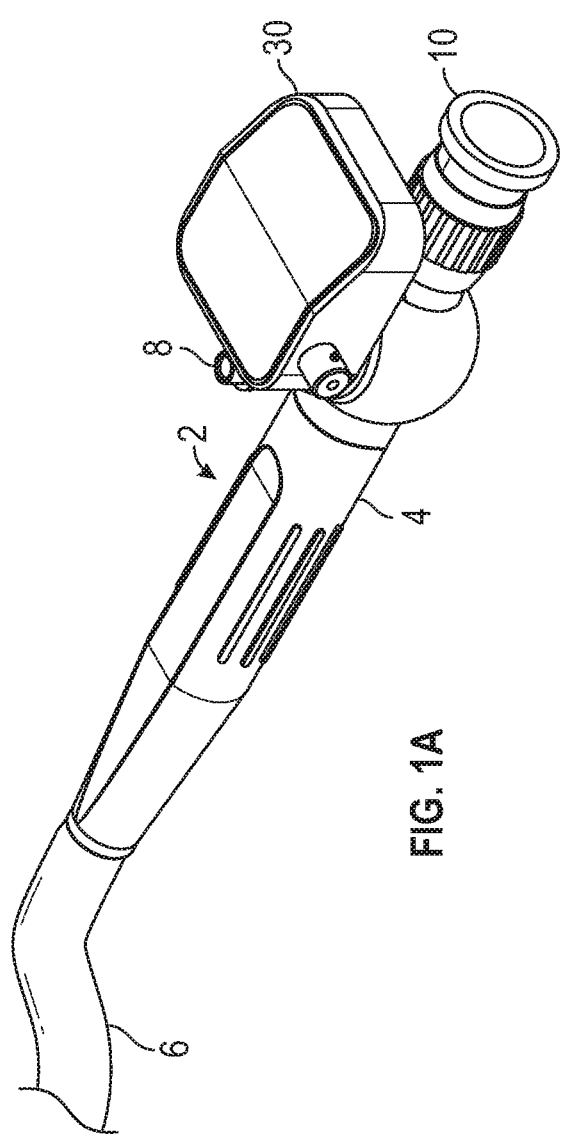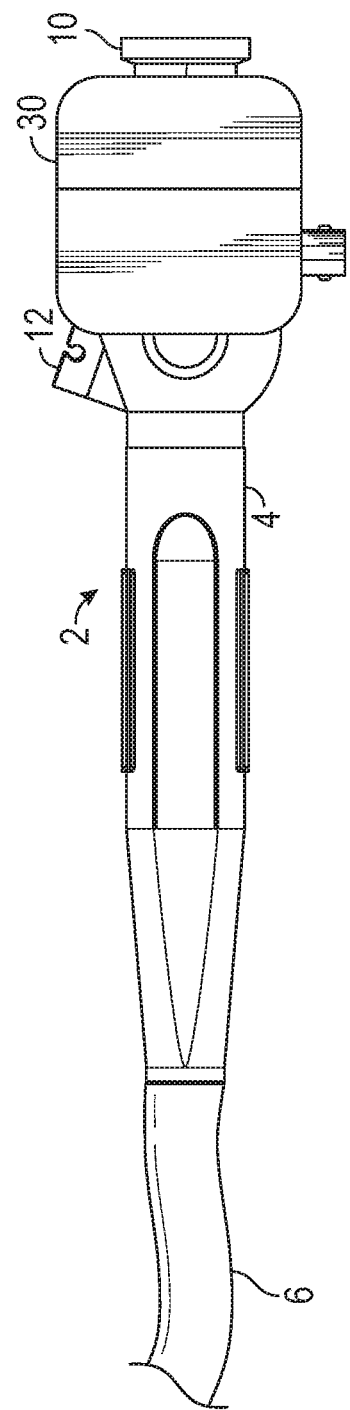
FIG. 1A
FIG. 1B

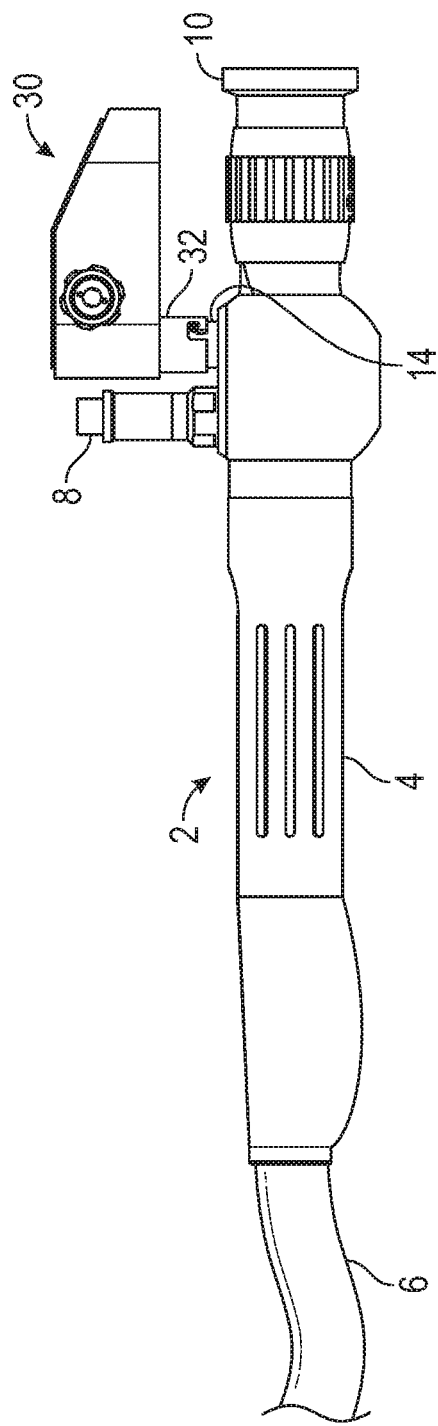
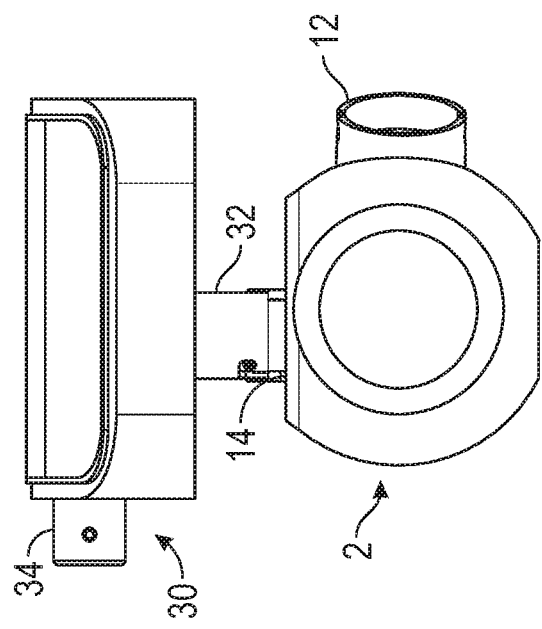
FIG. 1C
FIG. 1D

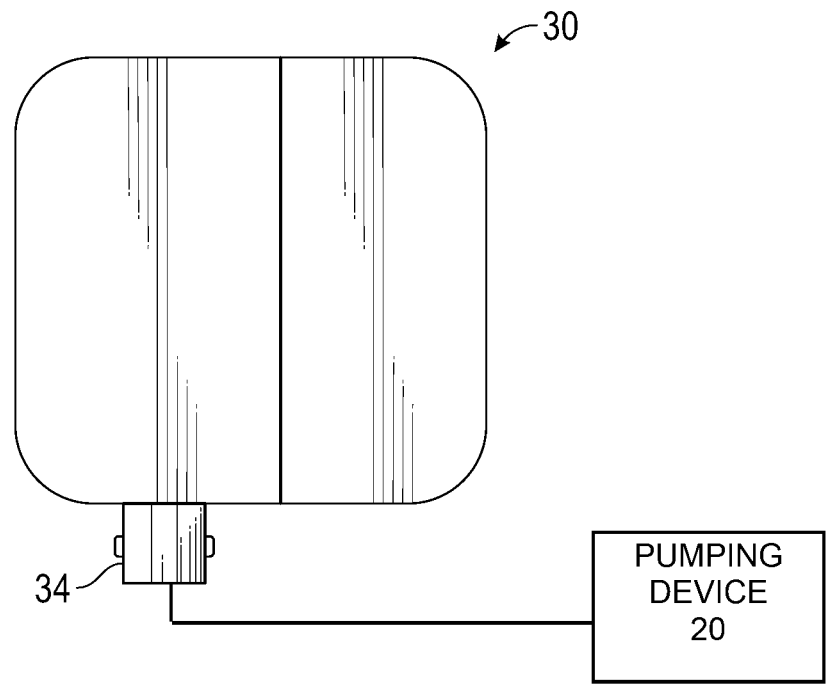
FIG. 2C
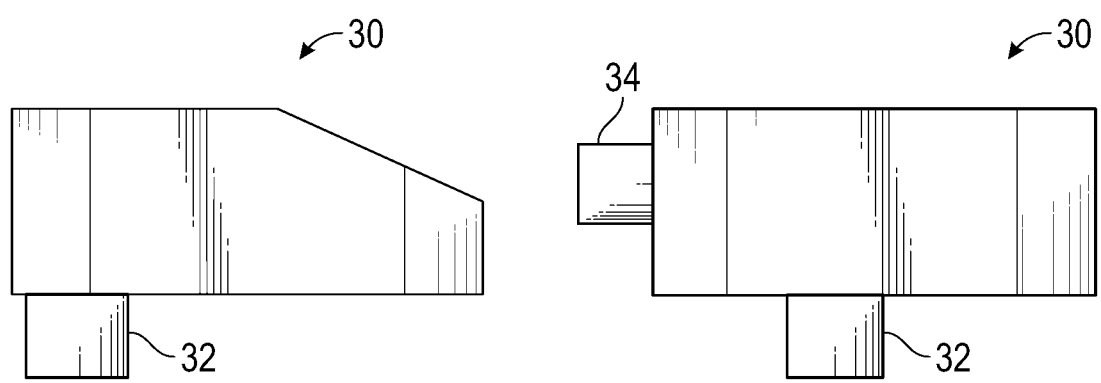
FIG. 2D  FIG. 2E

APPARATUS AND METHOD FOR MONITORING DIFFERENTIAL PRESSURE

CROSS-REFERENCE TO RELATED APPLICATIONS

This application claims the benefit of the priority date of U.S. Provisional Patent Application Ser. No. 62/474,648, titled APPARATUS AND METHOD FOR MONITORING DIFFERENTIAL PRESSURE, filed Mar. 22, 2017.

BACKGROUND

Field

This present disclosure relates generally to a pressure monitoring device coupled to a closed-cavity tool and, more particularly, to an apparatus and a method for monitoring pressure to detect a leakage-type failure of a medical device such as an endoscope by creating and monitoring a differential pressure to the external atmospheric pressure.

Discussion

An endoscope is an illuminated optical, typically slender and tubular instrument used to look deep into the body and used in a procedure called an endoscopy. Different types of endoscopes have been developed to be used in different parts of the body—such as the esophagus, the colon, and other places. Endoscopes serve a valuable function, allowing doctors to visualize internal parts of the body without surgical incision, and further allowing the collection of tissue specimens (biopsies) for testing. As a result of the biopsy testing and visual information collected, the doctor can determine an appropriate course of treatment for the patient.

The entirety of an endoscope—including a structural body at the proximal end (in the doctor's hand) and the flexible tubular distal portion—is closed, forming a sealed internal volume. The formation of a puncture or leak at any location in the endoscope—particularly in the tubular portion which has been inserted into the patient—would allow the patient's bodily fluids to enter the internal volume of the endoscope, and allow any material inside the endoscope to escape into the patient's body. Because it is impossible to guarantee that the interior of an endoscope is sterile, especially after multiple usages, it is most desirable to avoid such leakage.

By definition, a leaking endoscope cannot be effectively sterilized or high-level disinfected, and would never knowingly be used on a patient. Medical service providers typically leak-test endoscopes during the sterilization process, after the scope is used in one procedure and before the scope is used in another procedure. However, if cleaning and sterilization is undertaken with a leak present, the interior of the endoscope can be flooded with cleaning fluids or other chemicals, resulting in a much higher repair cost. Additionally, if the leak is left undetected and the endoscope is used in a procedure, the patient could be exposed to the chemicals or other harmful substances. Therefore, there is a need for real-time endoscope leak testing during a procedure so that, if a leak is detected, the doctor can terminate the procedure and remove the endoscope from the patient as quickly as practicable.

SUMMARY

In accordance with the teachings of the present disclosure, a pressure monitoring device is provided for use with a tool such as a medical endoscope. The device includes a housing which is fluidically coupled with an internal volume of the endoscope. A pump is used to change the pressure inside the device housing and endoscope, thereby establishing a pressure differential from the ambient environment. During an endoscopy procedure, the pressure inside the device housing is monitored, and a change in pressure exceeding a predefined limit causes an alarm signal indicating a leak has occurred in the endoscope. The device housing may be directly mounted to the endoscope, or located remotely and connected with a coupling tube. The pump may be integrated internally to the device housing, or it may be a separate external pump which is connected to the housing. The pressure differential may be positive or negative relative to ambient.

Additional features of the presently disclosed methods and devices will become apparent from the following description and appended claims, taken in conjunction with the accompanying drawings.

BRIEF DESCRIPTION OF THE DRAWINGS

FIG. 1A is a perspective view illustration of an endoscope having a pressure monitoring control module according to the invention mounted thereon;

FIG. 1B is a top plan view of the endoscope with the control module shown in FIG. 1A;

FIG. 1C is a side elevation view of the endoscope with the control module shown in FIG. 1A;

FIG. 1D is an end view of the endoscope with the control module shown in FIG. 1A;

FIG. 2C is a top plan view of the control module shown in FIG. 2A;

FIG. 2D is a side elevation view of the control module shown in FIG. 2A;

FIG. 2E is an end view of the control module shown in FIG. 2A;

DETAILED DESCRIPTION OF THE EMBODIMENTS

The following discussion of the embodiments of the disclosure directed to an apparatus and method for monitoring differential pressure is merely exemplary in nature, and is in no way intended to limit the disclosed devices or their applications or uses. For example, the invention is described in the context of an endoscope, but is anticipated to be useful with tools of many types. In respect of the methods disclosed, the steps presented are exemplary in nature, and thus, steps may be added, removed or reordered without departing from the spirit and scope of the invention.

As discussed above, there is a need for real-time endoscope leak testing during a procedure so that, if a leak is detected, the doctor can terminate the procedure and remove the endoscope from the patient as quickly as practicable. The apparatus according to the invention uses an innovative means of detecting failure of a tool, such as a medical endoscope, by creating and monitoring a differential pressure to the external atmospheric (ambient) pressure. After the differential pressure is established, any significant change to the fluid/gas pressure inside the endoscope indicates a leak has developed and a cross contamination potential exists, and the monitoring device immediately notifies the person or system operating the tool of the potential problem. The indication can be any form of light, sound, electronic communication or otherwise.

Two main embodiments of the invention are disclosed below. A passive embodiment of the device does not include a built-in means for establishing a pressure differential between the interior of the endoscope and the environment. The passive embodiment must be attached to an external pump which creates the pressure differential. An active embodiment of the device includes an integral internal piston assembly and a power source, and can create the desired pressure differential without the need for connecting to an external pump. Either the passive or the active embodiment may further be configured to be directly mounted in or on the endoscope, or located remotely from the endoscope and connected by a small tube or hose.

Figure 6:
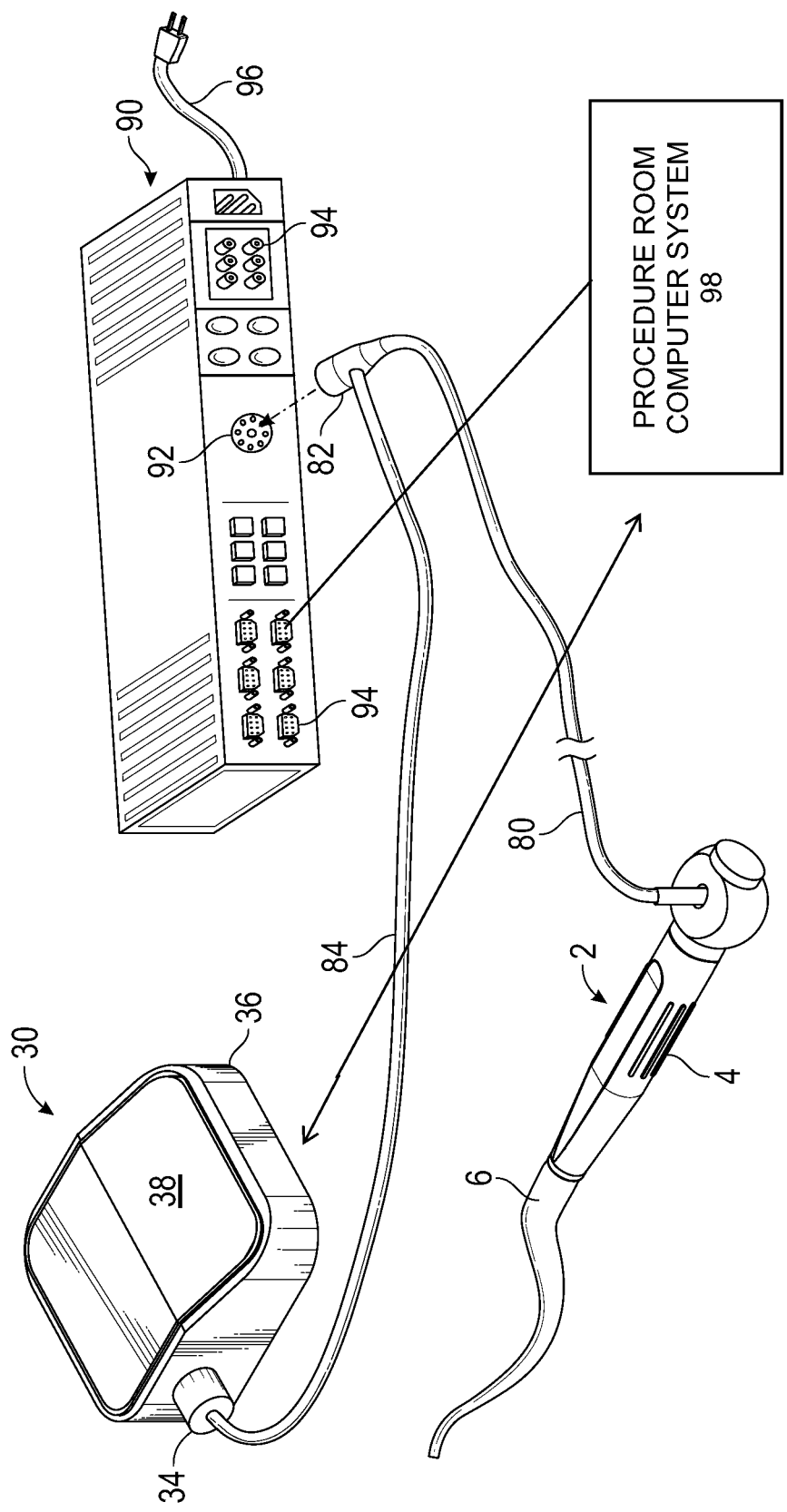
FIG. 6 is an illustration of a pressure monitoring control module located remotely from the endoscope and connected to the endoscope by a hose.

There is shown in FIGS. 1A-1D a tool 2 to which a pressure monitoring control module 30 according to the invention is mounted. In FIGS. 1 and 6, and all of the following discussion, the tool 2 is specifically an endoscope. The tool 2 includes a body 4, which is a structural component made of a suitable metal or plastic. The body 4 is generally tubular and hollow. At a distal end of the body 4, meaning the end of the body 4 which is situated away from the doctor, is affixed a flexible tube 6. The tube 6 is the component of the tool 2 which is inserted into the patient— for example, down the esophagus toward the stomach. The tube 6 is much longer than shown in the figures as its detail is not significant to the discussion, other than to point out that the distal end of the tube 6 is sealed, such as with a lens through which fiber optic elements can illuminate and view, or a video camera element.

The endoscope (tool 2) shown in FIG. 1 is an optical endoscope, with an eyepiece and fiber optics (discussed below) for illumination and viewing. Another type of endoscope, which is increasing in popularity, is a video endoscope (discussed later in reference to FIG. 6). In a video endoscope there is no eyepiece; instead, a digital video camera is located at the distal end of the flexible tube 6, and digital video images are provided by electrical/electronic connection to an external video processor for display on a display device. The disclosed leak testing technique using the control module 30 is applicable to both optical and video endoscopes.

At a location near the middle of the body 4, an adapter 8 is provided, where the adapter 8 is configured for attachment of a light source to provide illumination via light fibers into the body cavity being examined. At a proximal end of the body 4, an eyepiece 10 is provided, where the eyepiece 10 allows attachment of a video camera or other means of viewing the body cavity via optical fibers which extend all the way to the distal end of the flexible tube 6. The tool 2 also includes a port 12 configured to accept a biopsy tool (not shown), where the port 12 provides access to a secondary internal tubular passage (not shown) through which the biopsy tool can be extended to the distal end of the flexible tube 6 to take a tissue sample from the patient.

The above discussion of the tool 2 (endoscope) is provided for background information only. The main point is that the body 4 and the flexible tube 6 are sealed at both ends and at all other ports, resulting in an internal volume which should be leak-free and air-tight at all times. Thus, only exterior surfaces of the tool 2 should ever be in contact with the patient, and only those exterior surfaces can be and must be sterilized or high-level disinfected before a procedure.

As discussed above, it is undesirable for a leak to develop in the tool 2 during a patient procedure. However, it can easily be imagined that a leak or puncture could occur, in the flexible tube 6 for example, during a procedure. It is even more undesirable for a leak to develop and go undetected, as the continued use of the tool 2 exposes the patient to greater potential cross contamination with material inside the tool 2. Until now, doctors had no way to determine if a leak had developed during a procedure.

Figure 2A:
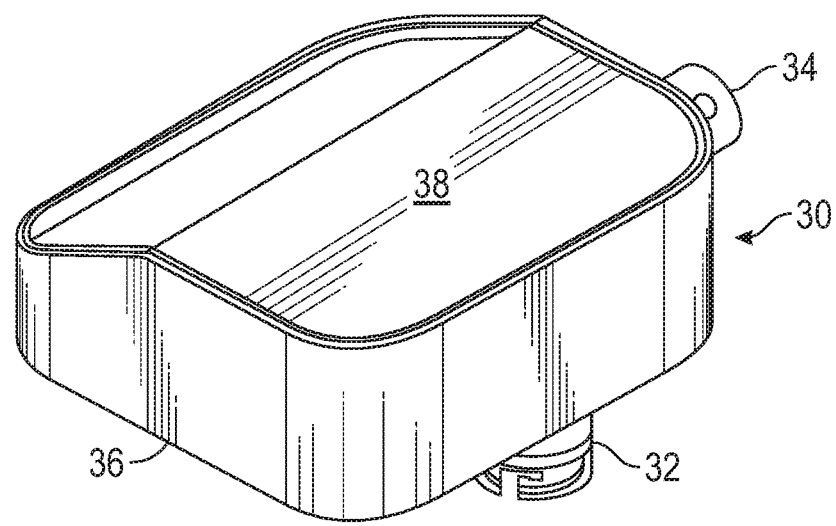
FIG. 2A is a perspective view illustration of the pressure monitoring control module shown in FIG. 1A.
Figure 2B:
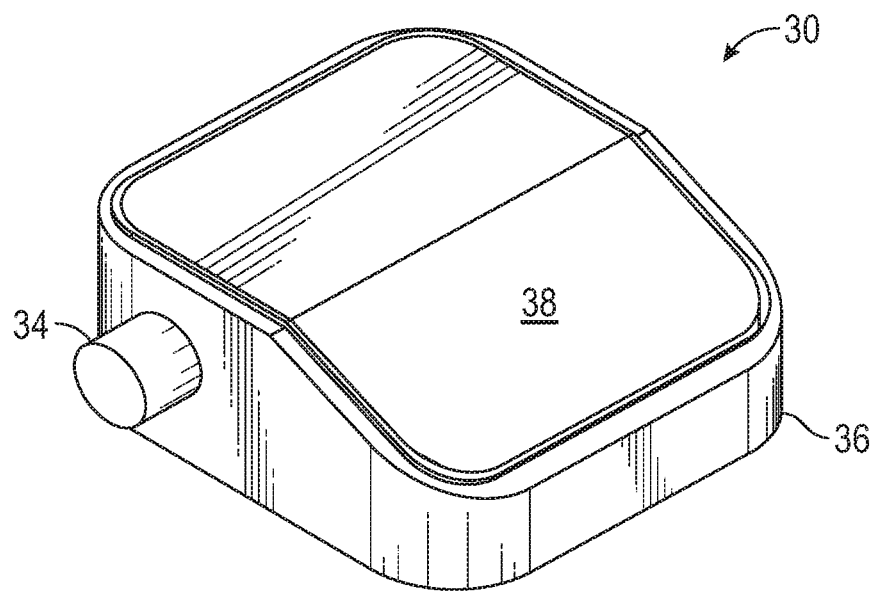
FIG. 2B is a reverse perspective view of the control module shown in FIG. 2A.

The pressure monitoring control module 30 provides the leak detection capability discussed above. The control module 30, shown without the tool 2 in FIGS. 2A-2E, is in fluid communication with the internal volume of the tool 2 through an outlet port 32 (FIG. 2A) which is coupled to a corresponding pressure port 14 on the body 4 of the tool 2. When the control module 30 is coupled to the tool 2, this causes the internal pressures to become equal but unknown relative to the atmospheric pressure outside the tool 2 and control module 30. A means for changing air pressure, such as a pumping device 20 shown in FIG. 2C, is then connected to an accessory port 34 (FIGS. 2A-2C) of the control module 30. After the pumping device is activated, the pressure inside the control module 30 and the tool 2 is changed to a pressure at the desired difference relative to atmospheric pressure. At this point, a signal is provided to indicate that the desired differential pressure has been established and leak detection capability is operational via pressure monitoring.

The differential pressure of the combined internal volume (of the control module 30 and the tool 2) relative to ambient may be positive or negative. In other words, the combined internal volume may be pressurized slightly, or the combined internal volume may be pumped out to a partial vacuum. In a preferred embodiment, the pressure differential is a partial vacuum in the combined internal volume of the control module 30 and the tool 2, and the pressure difference is about ⅓ of atmospheric pressure. In other words, if the ambient pressure in the procedure room is a standard atmosphere of 14.7 psi, then the absolute pressure in the combined internal volume will be established at about 10 psi (which is about ⅓ less than 14.7). Once the desired pressure differential is established, the pumping device is turned off and the pressure in the combined internal volume should remain at the desired value as long as there are no leaks.

By establishing the differential pressure as described above, any leak or puncture in the tool 2 will immediately be made apparent by a change in the pressure in the combined internal volume. In the example described above, where the combined internal volume of the control module 30 and the tool 2 has an initial absolute pressure of 10 psi, if a leak develops in the tool 2, the pressure in the control module 30 will rise from 10 psi to near ambient pressure of 14.7 psi. During pressure monitoring, some slight variation from the 10 psi value is allowable without signaling an alarm, to account for temperature change of the flexible tube 6 when inserted into the patient, for example. However, any increase in pressure greater than about 10%, or 1 psi, for example, can be considered a definite indication of a leak. This pressure monitoring leak detection technique is only effective when a differential pressure is first established, as in the embodiments of the present invention.

Any suitable design for the control module 30 may be used, as long as the device is air-tight and capable of monitoring a change in internal pressure. The control module 30 as shown in FIGS. 2A-2E has a case 36 or bottom portion that is cup-shaped and covered by a top 38 to form an enclosed housing for components. The accessory port 34 and the outlet port 32 extend through the walls of the case 36, allowing fluid communication with the pumping device and the tool 2, respectively.

Figure 3A:
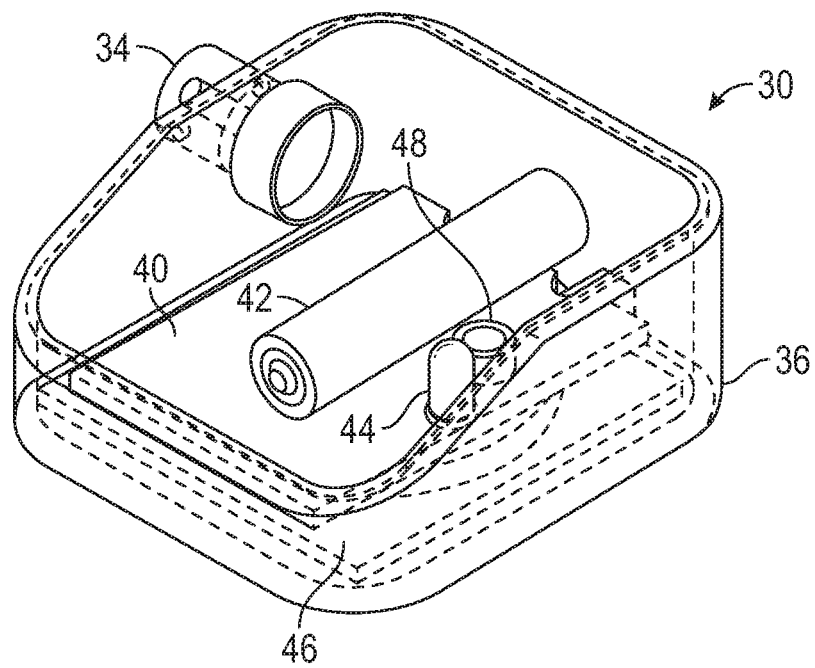
FIG. 3A is a cutaway perspective view similar to FIG. 2A of a first embodiment of the pressure monitoring control module.
Figure 3B:
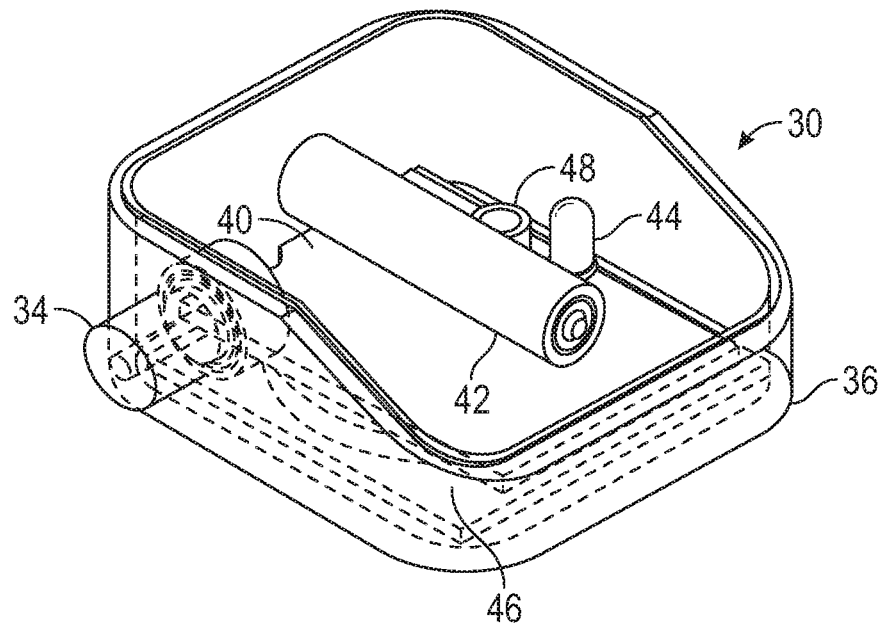
FIG. 3B is a reverse cutaway perspective view of the control module shown in FIG. 3A.

The components inside the housing of the first or passive embodiment of the control module 30 are shown in FIGS. 3A and 3B. A printed circuit board (PCB) 40 is positioned in the bottom of the case 36. The PCB 40 is an exemplary representation for any suitable type of processor that may be used in the control module 30. Instead of the PCB 40, an application specific integrated circuit (ASIC), a general purpose microprocessor, or any other suitable processing or computing device may be used. Mounted on or connected to the PCB 40 are a battery 42, an LED 44, an optional wireless charging coil 46 and a pressure sensor module 48. The battery 42 provides power to the components in the control module 30—including the PCB 40, the LED 44 and the pressure sensor module 48.

The LED 44 is an indicator that provides communication to the operator through different output states. The LED 44 is representative of any and all types of outputs that may be desired from the control module 30. The outputs can be any modality or combination of modalities: optical (such as by the LED 44); audible; wirelessly transmitted; or hard wired. Optical and audible outputs may be provided directly by the control module 30. Output signals may also be provided from the control module 30 to a monitoring system which is in use in the procedure room. That is, the monitoring system in the procedure room would typically have its own built-in data recording system, audible alarms, visible alarms, etc. Outputs from the control module 30 would be compatible with and usable as inputs to the procedure room monitoring system.

To use the control module 30 for leak detection by pressure monitoring, the control module 30 is first coupled to the tool 2 as described above. Then the pumping device is activated to create the differential pressure between the combined internal volume (of the module 30 and the tool 2) and the outside environment, as discussed above. When an acceptable internal pressure (such as 10 psi absolute) is reached, the LED 44 displays a signal, such as a green light, indicating the acceptable differential pressure. Once set, the LED 44 will continue to display the signal indicating proper tool pressure. If the sensed pressure changes outside set limits, then the LED 44 signals an alarm condition indicating a change in pressure and a possible leak in the tool 2. As mentioned, the "operative/normal" signal and the "alarm" signal may be displayed by the LED 44, produced audibly by the control module 30, and/or provided by electronic communication from the control module 30 to the procedure room monitoring system.

The pressure sensor module 48 monitors pressure continuously when the control module 30 is in operation—first determining when the acceptable pressure differential has been established, and then monitoring the internal pressure to detect changes. In monitoring mode, the control module 30 allows for some variations in the pressure signal from the pressure sensor module 48 without setting off the alarm signal. The normal acceptable pressure variations may be due to temperature changes in the tool 2 when advanced into the patient's body, and slight volume changes caused by bending and unbending of the flexible tube 6 of the tool 2. The control module 30 triggers the alarm should the pressure change too quickly or outside preset parameters. For example, if the internal pressure climbs from the 10 psi starting value, the alarm may be triggered when the internal pressure reaches a threshold value of 11 psi.

Rate of pressure change is also monitored and may trigger an alarm, where the rate of pressure change detection allows for the possibility of contamination plugging a leak prior to the internal pressure reaching the alarm threshold. For example, if the internal pressure climbs from 10 psi to 10.8 psi within a few seconds, the alarm may be triggered due to the high rate of pressure change, even though the alarm pressure threshold (e.g., 11 psi) is not exceeded because the leak is temporarily plugged by a contaminant.

When a leak is detected and the alarm is triggered, the control module 30 may be configured to release the differential pressure, so that the interior of the endoscope quickly returns to ambient pressure. Alternately, the control module may not mechanically release the differential pressure, but instead just allow the interior pressure to return to ambient due to the leak. The alarm can be disabled or reset by the operator. Even if the operator decides to immediately discontinue the procedure upon notice of a leak, he or she may not want to continue to hear the alarm signal while removing the endoscope from the patient, so disabling or silencing the alarm is a desirable feature. The operator of the tool 2 may also determine that it would not be desirable to immediately discontinue the procedure, in which case the ability to silence the alarm is even more essential. Any time a leak is detected while the endoscope is inside a patient, the operator can choose to take immediate remedial action with the patient, or make note of follow-up action or monitoring which is to be undertaken.

The control module 30 also provides the option to re-establish the pressure differential and restart leak detection monitoring. In this case, the pumping device would again be activated to create the differential pressure between the combined internal volume (of the module 30 and the tool 2) and the outside environment, as discussed above. Upon signaling that the desired differential pressure has been achieved, the procedure can resume with active leak detection monitoring, and the operator can choose to continue or discontinue the procedure based upon how soon a second leak alarm is issued.

Power for the control module 30 is supplied by the battery 42 that is rechargeable through the wireless charging coil 46 when in the presence of an external charging system. In some versions, the control module 30 could be disposable and the wireless charging coil 46 would then not be present. The battery 42 may also be a single-charge disposable type, even if the control module 30 itself is reusable many times; in this case the charging coil 46 is not needed. In another embodiment, an external power supply could provide power to the control module 30 via an electrical cable, and the battery 42 would not be needed.

A check valve or shut-off valve may be provided between the external pumping device and the control module 30—near the accessory port 34. The check valve or shut-off valve would prevent pressure leakage through the accessory port 34 after the differential pressure is established and the pumping device is turned off.

Other types of sensors besides the pressure sensor module 48 may also be included in the control module 30. For example, a humidity sensor 48 may be provided inside the control module 30, and a baseline humidity level could be measured once the control module 30 is coupled to the tool 2. Then, during the endoscopic procedure, any significant change in humidity level would trigger the alarm signal indicating a potential leak. A moisture sensor 48 may also be provided, either instead of or in addition to the humidity sensor. It is possible that in some circumstances the humidity sensor 48, or another type of sensor, may detect a change of conditions inside the control module 30—indicative of a leak in the tool 2—sooner than the pressure sensor module 48. In summary, the sensor 48 shown in FIGS. 3A and 3B can be one or more of a pressure sensor, humidity sensor and a moisture sensor.

Figure 4A:
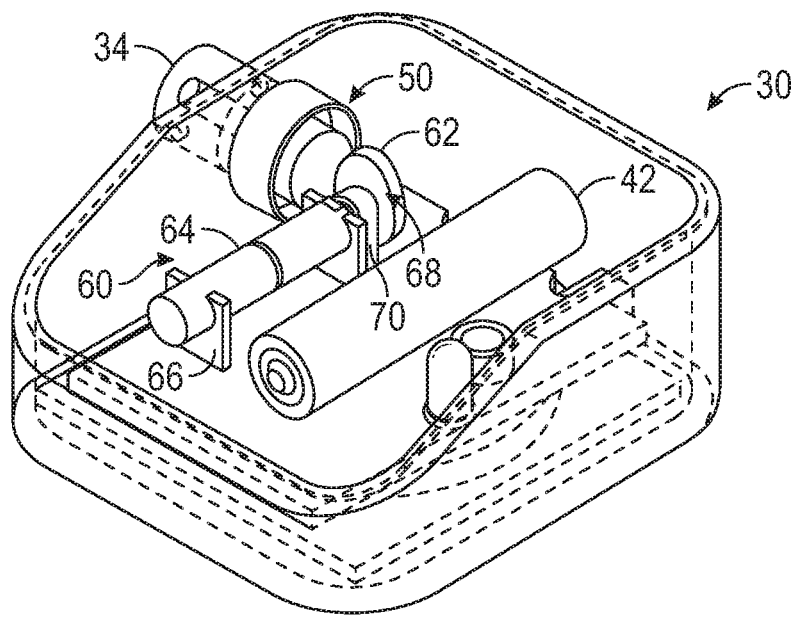
FIG. 4A is a cutaway perspective view similar to FIG. 2A of a second embodiment of the pressure monitoring control module.
Figure 4B:
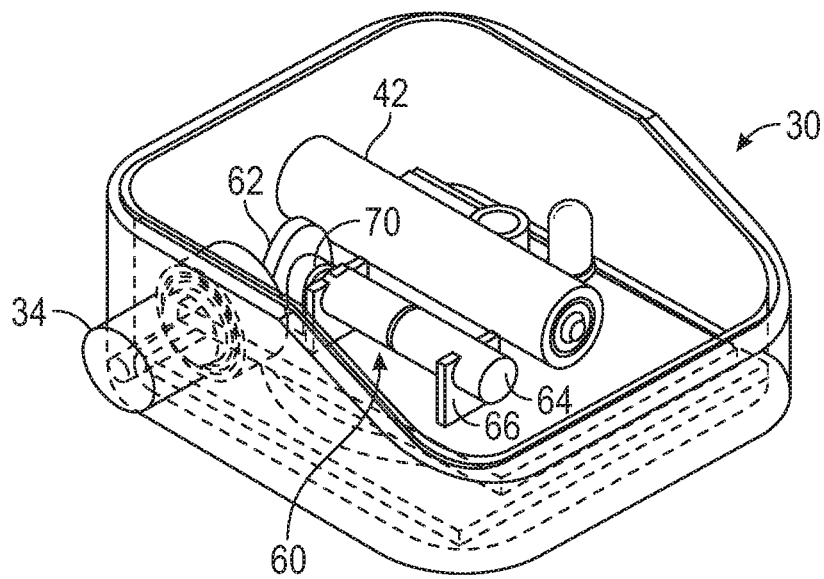
FIG. 4B is a reverse cutaway perspective view of the control module shown in FIG. 4A.
Figure 5:
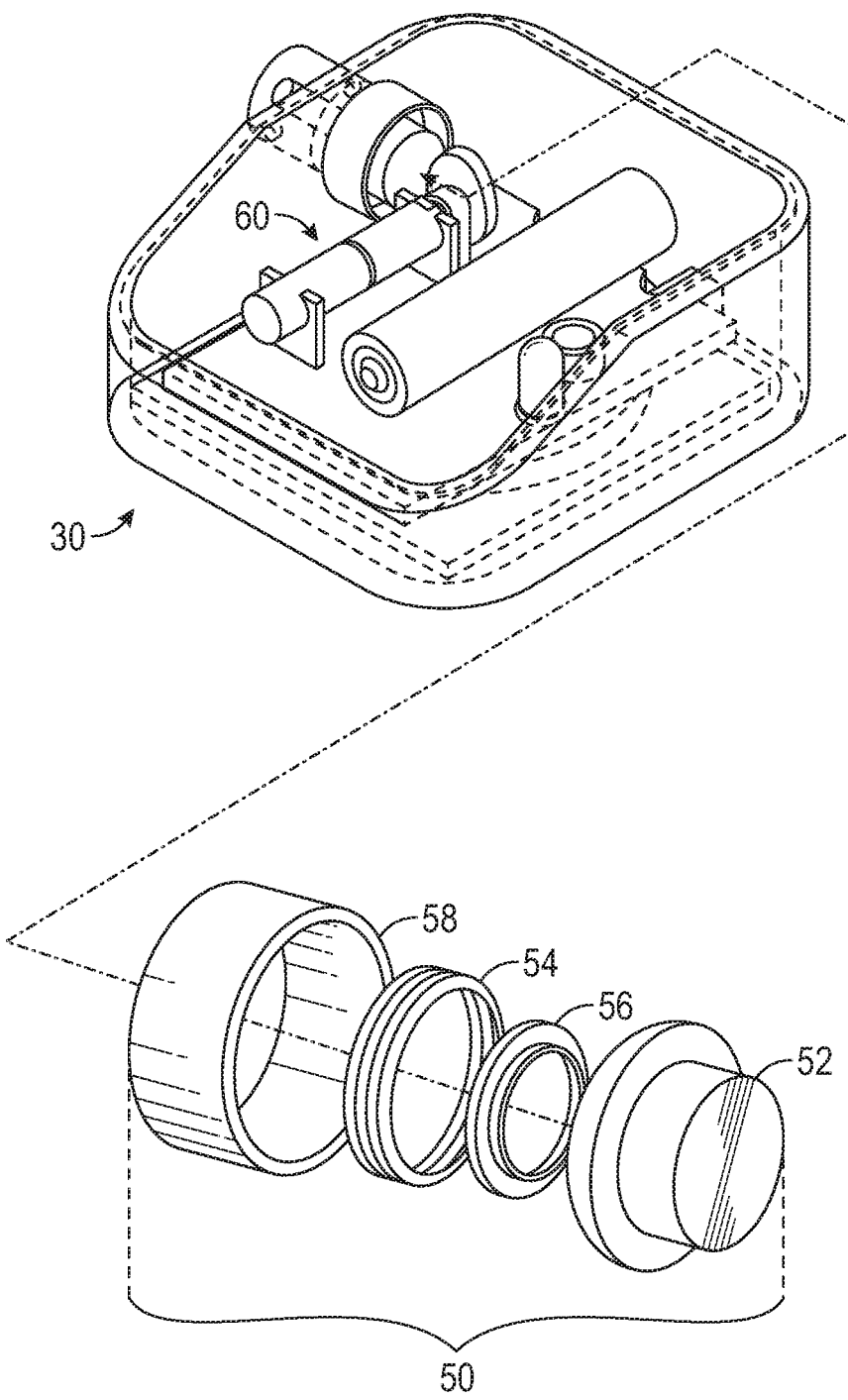
FIG. 5 is an exploded perspective view of the piston assembly in the second embodiment of the control module shown in FIG. 4A.

The second embodiment of the control module 30 according to the invention is an active embodiment and is shown in FIGS. 4A, 4B and 5. The active embodiment functions identically to the passive embodiment with one exception; an internal piston assembly is added to the active embodiment, thus eliminating the need to connect to an external pumping device as discussed above for the passive embodiment. The addition of the piston assembly in the active embodiment enables the control module 30 to modify the internal pressure to a level different enough to allow sensing of a leak anywhere within the monitored cavities.

The active embodiment of the control module 30 has a piston assembly 50 which includes a piston 52, a compression spring 54, a check valve 56 and a piston cavity 58. The piston assembly 50 is shown in exploded form in FIG. 5. The control module 30 also has a drive assembly 60 that includes a cam 62, a planetary DC motor 64 and a motor mount 66. The motor 64 rotates an axle 68 in an axle support 70. The cam 62 is attached to the axle 68 for rotation by the motor 64. When the control module 30 is commanded to begin and establish the differential pressure, the motor 64 rotates the axle 68 (and therefore the cam 62) by a quarter turn or a half turn. The non-symmetric form of the cam 62 presses against the piston 52 to move the piston 52. If the piston 52 is moved outward (away from the axle 68) by the cam 62, the volume inside the control module 30 will increase and the pressure inside the control module 30 will drop. If the cam 62 is rotated to allow inward movement of the piston 52, the spring 54 pushes the piston 52 inward to decrease the volume and increase the pressure inside the control module 30. The piston assembly 50 can be configured to increase or decrease internal pressure by selecting the check function of the check valve 56.

The PCB 40 in the control module 30 can be provided with one or more communication components to communicate data and track performance of the tool 2. These communication components can be optical, wired, wireless and/or any other means of communication between two devices. Thus, the components of the control module 30 can send and/or receive signals through the communication component(s) to and from a data processing device such as a computer as would be used in an endoscopy procedure room. This includes the ability to log performance of the tool 2 over a timed interval made retrievable through any of the aforementioned techniques.

While the pressure monitoring control module 30 has been described above and shown in FIGS. 1A-1D as an external tool-mounted configuration, other embodiments are possible. In one alternate embodiment, the control module 30 can be miniaturized for integrated mounting inside the tool 2, or mounted in an accessory device used with the endoscope. In another embodiment, the pressure monitoring control module 30 can be positioned remotely.

FIG. 6 is an illustration of a pressure monitoring control module 30 located remotely from the endoscope tool 2 and connected to the endoscope by fluid couplings discussed below. In FIG. 6, the tool 2 is a video endoscope of the type described earlier. In a typical video endoscope system, the endoscope (tool 2) is connected to a video processor 90 via an umbilical cord 80. The umbilical cord 80 provides electronic communication from the endoscope tool 2 to the video processor 90. The umbilical cord 80 may also include one or more fluid passages used for providing sterile water or other fluids to the distal end of the flexible tube 6.

At an end opposite the tool 2, the umbilical cord 80 terminates in a plug 82, which plugs into a jack 92 on the video processor 90. The video processor 90 also includes one or more ports 94 for communication with a separate computer, a video display device, or other electronic device, as understood by those skilled in the art. The ports 94 may be on an opposite side of the video processor 90 from the jack 92; they are shown on the same side in FIG. 6 for clarity and simplicity. The video processor 90 also includes a power cord 96 for providing electrical power.

The control module 30 depicted in FIG. 6 (shown much larger than scale) is the active embodiment of FIGS. 4 and 5, with its own internal pumping device. A hose 84 couples the accessory port 34 of the control module 30 with the plug 82 on the end of the umbilical cord 80. The differential pressure created by the control module 30 is communicated to the tool 2 via the hose 84 and a continuation of the hose 84 which is inside the umbilical cord 80. The hose 84 can be very small in diameter, as volume flow rate through the hose 84 is not an important factor. In the embodiment of FIG. 6, the tool 2 is not encumbered with any additional structural appendages, thus enabling easy manipulation of the tool 2 by the operator.

In any embodiment, and particularly in the embodiment shown in FIG. 6, the control module 30 can be connected to a procedure room computer system 98 for full two-way electronic communication—including sending signals (ready signal, alarm signal) from the control module 30, sending collected data from the control module 30, and sending signals from the procedure room computer system 98 to the control module 30, such as procedure begin and end signals, silence alarm signal, etc. The two-way communication between the control module 30 and the procedure room computer system 98 can be facilitated by wireless communication or by wires running along the hose 84 to the plug 82 and into the video processor 90. The collected data sent from the control module 30 to the procedure room computer system 98 may include date, start time, stop time, tool ID #, patient identification information, pressure vs. time data, and any other available data. In any of the embodiments discussed above, the control module 30 can be constructed to be reusable and/or disposable.

The distance between the video processor 90 and the tool 2 as shown in FIG. 6 is not to scale; the video processor 90 would be much farther distant from the tool 2 in relation to the sizes shown; that is, the umbilical cord 80 in reality is longer than shown in FIG. 6. Another configuration of the embodiment shown in FIG. 6 would incorporate the control module 30 into the video processor 90. This would allow the hose 84 to be eliminated, and the fluid communication between the control module and the endoscope would be directly through the umbilical cord 80 and the plug 82 to the jack 92. The control module 30 could also be integrated into other accessories used with the endoscope.

Figure 7:
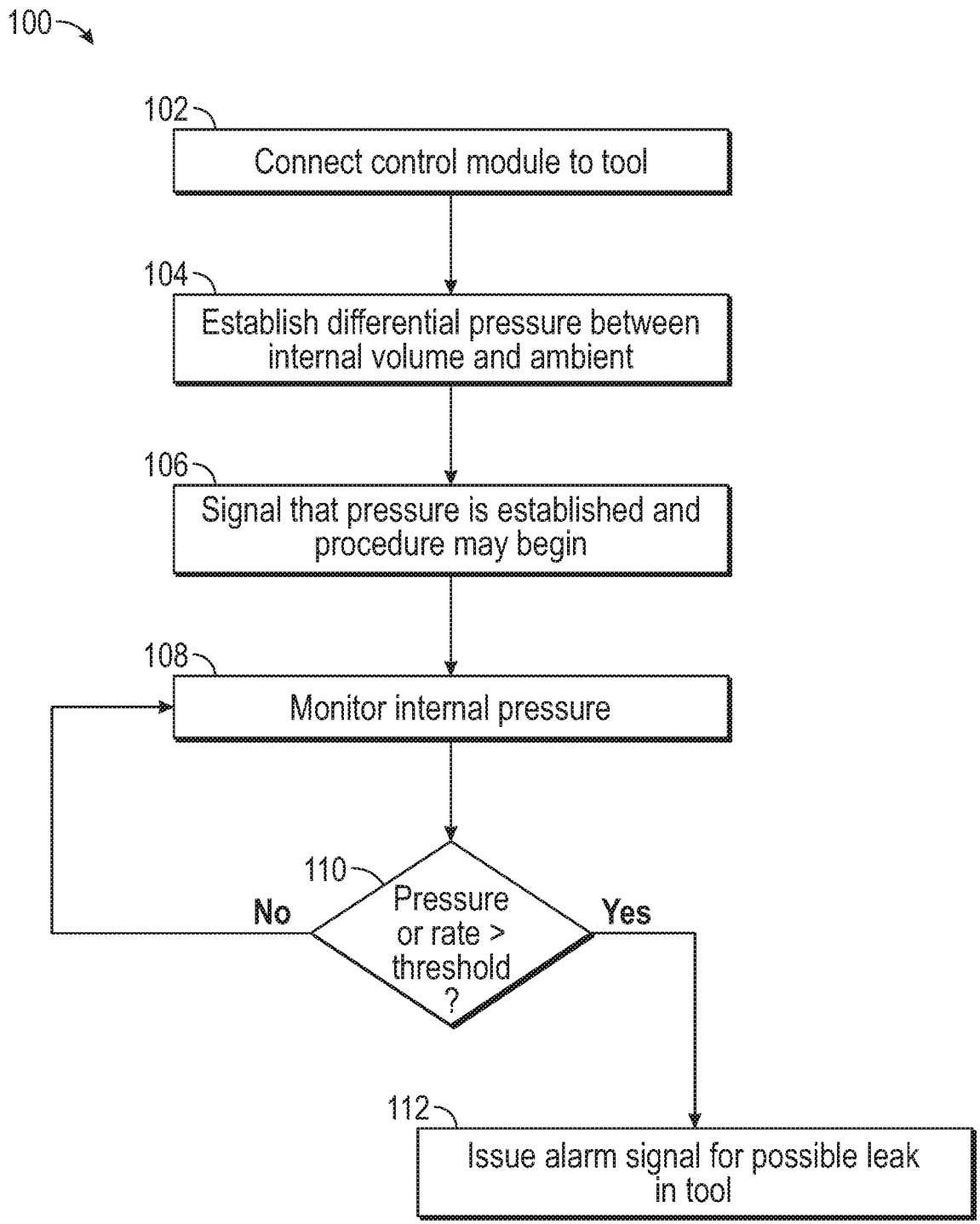
FIG. 7 is a flowchart diagram of a method for monitoring differential pressure in a tool to detect a leak, using the devices illustrated in FIGS. 1-6.

FIG. 7 is a flowchart diagram 100 of a method for monitoring differential pressure in a tool to detect a leak, using the devices illustrated in FIGS. 1-6. At box 102, the pressure monitoring control module 30 is connected to the tool 2 such that an internal volume of the control module 30 is in fluid communication with an internal volume of the tool 2 to create a combined internal volume. The control module 30 may be directly mounted upon the tool 2, or the control module 30 may be located remote from the tool 2 and connected with the hose 80.

At box 104, a pressure differential is established between the combined internal volume and the ambient pressure outside the tool 2 and the module 30. If an external pumping device is used, the pumping device can be switched on and off in a normal manner. If the active embodiment of the control module 30 is used, a start button may be provided on the control module 30, or a start signal can be provided from a computer in the procedure room if so connected. At box 106, a signal is issued by the control module 30 indicating that the differential pressure has been established. The signal may be a solid green display of the LED 44 on the control module 30, or an audible tone, or any sort of signal may be communicated to the computer in the procedure room. Also at the box 106, the baseline or starting pressure is stored for usage during the monitoring phase. In the example discussed earlier, the baseline pressure after establishing the differential pressure is 10 psi absolute. As discussed, the baseline pressure may be any suitable value which is different from the ambient pressure outside the tool 2 and control module 30—where the internal pressure may be higher or lower than the external pressure.

At box 108, the tool 2 is in use and the pressure in the combined internal volume is continuously monitored by the control module 30 using the pressure sensor module 48. At decision diamond 110, the control module 30 monitors both the change in the internal pressure itself and the rate of change of pressure, and can issue an alarm if either of these parameters exceeds a predetermined threshold. For example, a pressure rate of change greater than 0.5 psi/minute may trigger an alarm. Also, if the baseline pressure is 10 psi, then a pressure sensor reading greater than 11 psi (change from baseline >1 psi) may trigger an alarm. The alarm thresholds listed here are merely exemplary. Thresholds can be configured based on the exact type of endoscope being used and procedure being performed. Threshold values may be configured by communication from a procedure room computer to the control module 30, or configured directly in the control module 30.

When no alarm condition is detected at the decision diamond 110, the process loops back to the box 108 to continue monitoring internal pressure. When an alarm condition is detected at the decision diamond 110, an alarm is issued at box 112 indicating a possible leak in the tool 2. The alarm can be any combination of a change in the LED 44 (change of color, a flashing code, etc.), an audible alarm, and/or any signal that may be displayed by a procedure room computer system based on an alarm signal from the control module 30. The alarm may be silenced by the tool operator if so desired. The operator may also choose to restart pressure monitoring after an alarm, beginning with re-establishment of the differential pressure.

The apparatus and method disclosed above for monitoring differential pressure fulfill the need for real-time leak detection in endoscopes and other tools. The various embodiments—including active, passive, tool-mounted and remote—offer great flexibility in selecting a control module most suited to a particular application.

While a number of exemplary aspects and embodiments for a pressure differential monitoring leak testing device have been discussed above, those of skill in the art will recognize modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A leak-detecting apparatus that monitors a differential pressure in a closed-cavity tool, said apparatus comprising:
a closed-cavity housing with an outlet port configured for coupling the housing to the tool such that an internal volume of the tool is in fluid communication with an internal volume of the housing forming a combined internal volume;
means for changing air pressure inside the combined internal volume to establish a baseline pressure inside the combined internal volume which is 20-40% lower than an ambient pressure outside the tool and the housing;
a pressure sensor inside the housing; and
a processor configured to establish the baseline pressure using the means for changing air pressure, monitor the air pressure inside the combined volume using the pressure sensor during a medical procedure using the tool, and issue an alarm signal indicating a possible leak in the tool if the air pressure inside the combined volume changes from the baseline pressure by more than a threshold amount or a rate of change of the air pressure inside the combined volume exceeds a rate threshold.

2. The apparatus according to claim 1 wherein the housing is directly mounted upon the tool by coupling the outlet port of the housing with an inlet port of the tool.

3. The apparatus according to claim 2 wherein the means for changing air pressure inside the combined volume is a piston assembly inside the housing which changes a volume of the combined internal volume.

4. The apparatus according to claim 3 further comprising a drive assembly inside the housing, said drive assembly being configured to actuate the piston assembly to change the air pressure inside the combined volume.

5. The apparatus according to claim 1 wherein the housing is positioned remotely from the tool and coupled to the internal volume of the tool via a hose.

6. The apparatus according to claim 5 wherein the means for changing air pressure inside the combined volume is an external pumping device coupled to an accessory port on the housing.

7. The apparatus according to claim 1 wherein the processor is further configured to signal when the baseline pressure has been established so that an endoscopy procedure using the tool may begin.

8. The apparatus according to claim 1 wherein the alarm signal and a signal when the baseline pressure has been established are visual signals provided by an LED visible on an outside surface of the housing, audible signals, or a combination of audible and visual signals, and the alarm signal can be cancelled or silenced by an operator.

9. The apparatus according to claim 8 further comprising a humidity sensor or a moisture sensor inside the housing, where another alarm signal is issued upon detection of moisture or a change of humidity.

10. The apparatus according to claim 1 further comprising one or more communication channels enabling electronic communication between the processor and a computer providing supervisory control of the tool, where the communication channels include hardwired or wireless communication.

11. The apparatus according to claim 1 wherein the tool is a medical endoscope.

12. A leak-detection device for a medical endoscope, said device comprising a closed-cavity housing coupled to the endoscope to form a combined internal volume, means for establishing a negative differential pressure between inside and outside the combined internal volume, where the negative differential pressure is 20-40% lower inside the combined internal volume than outside, a pressure sensor inside the housing, and a processor inside the housing configured to establish the negative differential pressure and monitor air pressure inside the combined internal volume using the pressure sensor, and issue an alarm signal based on a change to the negative differential pressure.

13. The device according to claim 12 wherein the housing is directly mounted upon the endoscope by coupling an outlet port of the housing with an inlet port of the endoscope.

14. The device according to claim 12 wherein the endoscope is a video endoscope coupled to a video processor by an umbilical cord, and the housing is positioned remotely from the endoscope and coupled to an internal volume of the endoscope via a hose connected to and through the umbilical cord.

15. A method for detecting a leak in a closed-cavity tool, said method comprising:
  providing a differential pressure monitoring control module having a closed-cavity housing with an outlet port configured for coupling the housing to the tool;
  coupling the control module outlet port to the tool such that an internal volume of the tool is in fluid communication with an internal volume of the housing forming a combined internal volume;
  operating a means for changing an air pressure inside the combined internal volume to establish a baseline pressure inside the combined internal volume which is 20-40% lower than an ambient pressure outside the tool and the housing;
  monitoring the air pressure inside the combined volume using a pressure sensor inside the housing connected to a processor in the control module, the processor being configured to establish the baseline pressure using the means for changing an air pressure, monitor the air pressure inside the combined volume using the pressure sensor during a medical procedure using the tool, and issue an alarm signal indicating a possible leak in the tool; and
  issuing the alarm signal indicating a possible leak in the tool if the air pressure inside the combined volume changes from the baseline pressure by more than a threshold amount or a rate of change of the air pressure inside the combined volume exceeds a rate threshold.

16. The method according to claim 15 further comprising signaling when the baseline pressure has been established so that a procedure using the tool may begin.

17. The method according to claim 15 wherein the control module is mounted upon the tool via coupling ports, and the air pressure inside the combined volume is changed using a piston assembly inside the control module which changes a volume of the combined internal volume.

18. The method according to claim 15 wherein the control module is positioned remotely from the tool and coupled to the internal volume of the tool via a hose.

19. The method according to claim 15 wherein the tool is a medical endoscope.

20. A device for detecting a leak in a medical endoscope including during use of the endoscope to perform a medical procedure, the device comprising:
  a closed-cavity housing having an accessory port and an outlet port, each of the ports extending through a wall of the housing to allow fluid communication between an exterior of the housing and an internal volume of the housing, wherein the housing is adapted to be mounted directly on a body of an endoscope and coupled to the body with the outlet port to form a combined internal volume including the internal volume of the housing and an internal volume of the body;
  wherein the accessory port is adapted to be coupled to a means for establishing a differential pressure in the combined internal volume that is 20-40% lower than an ambient pressure outside of the endoscope and the housing;
  a pressure sensor inside the housing in the internal volume for measuring the differential pressure; and
  a processor inside the housing in the internal volume whereby when the housing is mounted on and coupled to the body and the differential pressure is established as a predetermined baseline differential pressure, the processor is configured to monitor the differential pressure measured by the pressure sensor while the endoscope is used to perform a medical procedure and to issue an alarm signal based on a change of the differential pressure from the baseline differential pressure that exceeds at least one of a predetermined threshold amount and a predetermined rate of change.

* * * * *